United States Patent [19]

Hollister

[11] Patent Number: 5,615,771
[45] Date of Patent: Apr. 1, 1997

[54] SAFETY NEEDLE CARTRIDGE SYSTEM

[75] Inventor: William H. Hollister, Nelson, N.H.

[73] Assignee: Smiths Industries Medical Systems, Inc., Keene, N.H.

[21] Appl. No.: 43,890

[22] Filed: Apr. 7, 1993

Related U.S. Application Data

[63] Continuation-in-part of Ser. No. 884,191, May 18, 1992, abandoned.

[51] Int. Cl.$^6$ .............. B65D 83/10; A61M 5/32; A61M 5/00
[52] U.S. Cl. .............. 206/368; 604/192; 604/263
[58] Field of Search .............. 206/365; 604/192, 604/198, 263

[56] References Cited

U.S. PATENT DOCUMENTS

| | | | |
|---|---|---|---|
| 2,004,050 | 6/1935 | Kirk | 206/365 |
| 4,671,408 | 6/1987 | Raines et al. | 220/324 X |
| 4,820,277 | 4/1989 | Norelli | 604/192 |
| 4,872,552 | 10/1989 | Unger | 206/365 |
| 4,921,096 | 5/1990 | McFarlane | 206/365 X |
| 4,927,018 | 5/1990 | Yang et al. | 206/365 |
| 4,966,591 | 10/1990 | Yuen | 206/365 X |
| 4,982,842 | 1/1991 | Hollister | 206/365 |
| 5,154,285 | 10/1992 | Hollister | 206/365 |

FOREIGN PATENT DOCUMENTS

WO91/09638  7/1991  WIPO.

Primary Examiner—BethAnne C. Dayoan
Attorney, Agent, or Firm—Pollock, Vande Sande & Priddy

[57] ABSTRACT

A needle protection safety package, instead of being enclosed in a pouch or other containment wrappings, has fitted thereto at respective ends thereof caps or sheaths so that both the needle and the end to which a syringe is adapted to mate remain enclosed and sterile. Such an arrangement enables easy transport of the safety needle package and provides convenience for the user at the same time. The safety package is further designed to prevent burring of the tip of the needle as the cap or sheath is removed from the needle portion of the package. A further embodiment of the safety package incorporates a locking mechanism which prevents contact between the needle and the housing as the housing is pivoted to envelop the needle after use.

10 Claims, 6 Drawing Sheets

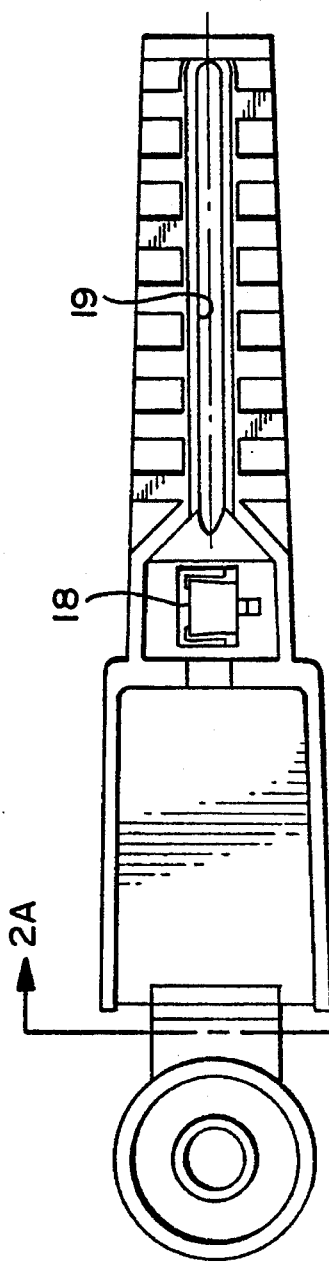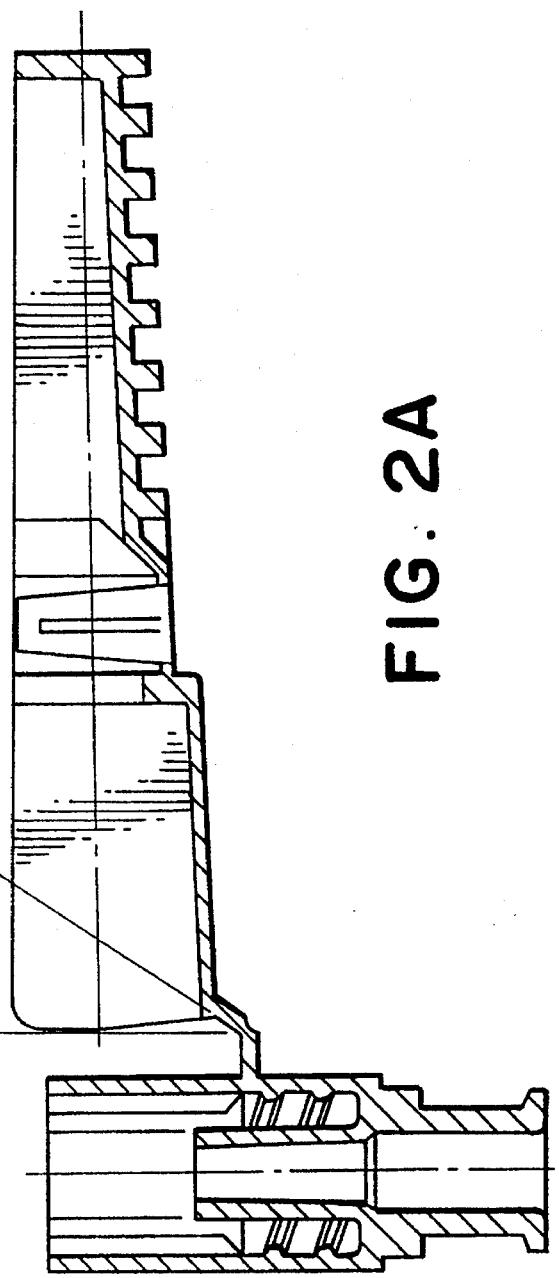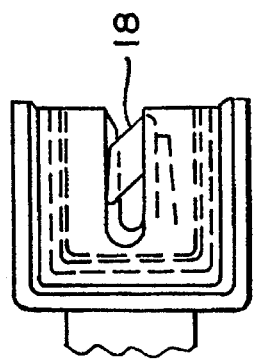

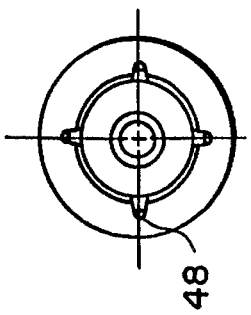
FIG. 3C
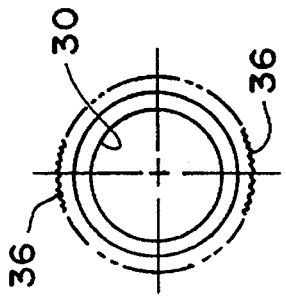
FIG. 4C
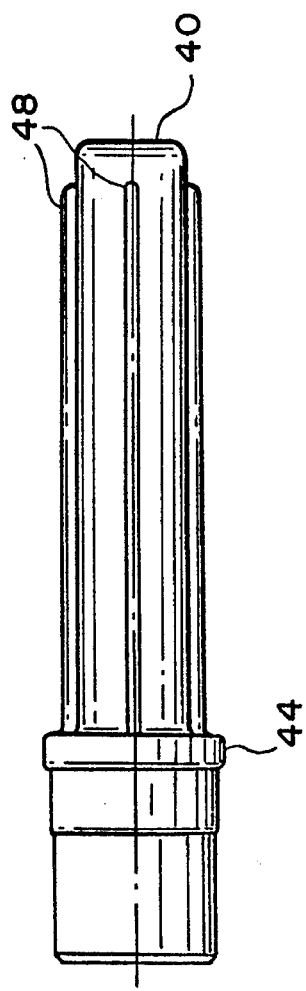
FIG. 3A  FIG. 3B
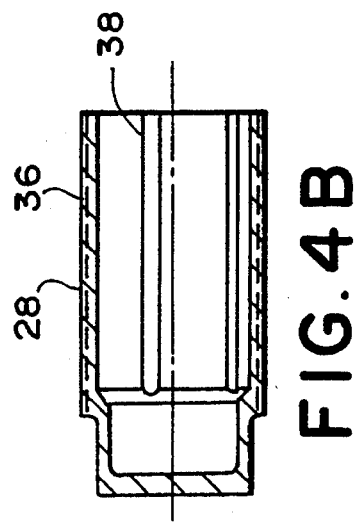
FIG. 4A  FIG. 4B
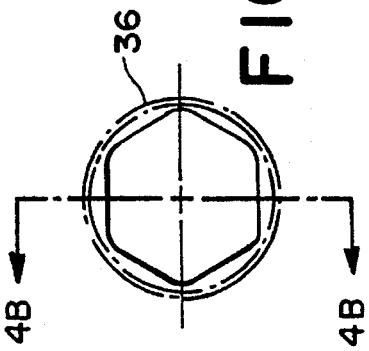

SAFETY NEEDLE CARTRIDGE SYSTEM

This is a continuation-in-part application of application Ser. No. 884,191 filed May 18, 1992, now abandoned.

FIELD OF THE INVENTION

The present invention relates to needle protection devices and more particularly to a convenient to use safety needle package.

BACKGROUND OF THE INVENTION

In a medical emergency, time is of the essence. For example, medical personnel have to quickly assemble a syringe to a needle for injecting medicant to a patient. With the recent onslaught of contagious diseases, to safeguard medical personnel, and bystanders, needle protection devices have been added to prevent unwanted needle sticks. Such incorporation of needle protection devices to the needle and syringe requires additional time.

A particular needle protection device having a needle integrated to a base, which in turn has connected thereto a pivotable housing, is disclosed in Landis U.S. Pat. No. 4,664,259. To maintain sterility for the device, in one of the embodiments, a frangible strip is provided to seal the housing to the base so that, in order to use the device, the frangible strip has to be peeled away and the housing pivoted away from the needle. This embodiment does not provide a sterile luer to which the syringe is mated. A second embodiment of the Landis invention shows the wrapping of the needle protection device in a sealed plastic pouch. Thus, a user has to tear the pouch to get to the device. As is well known, such pouches are oftentimes difficult to tear, particularly when they have been designed to be sufficiently strong to prevent accidental tearing. Accordingly, precious seconds may be wasted in removing the Landis device from its containment pouch. So, too, such pouch packages are bulky and medical personnel do not like to carry more than the minimum with them.

At the present time, another needle protection device sold in a pouch is the NEEDLE-PRO™ manufactured by the assignee of the present invention. From experience, it has been found that, in certain circumstances, the encasement of such needle protection device in a pouch, or other types of containment wrapping, is inconvenient.

SUMMARY OF THE PRESENT INVENTION

To provide both convenience and sterility, the present invention safety package (cartridge) has a base having a first end adapted to mate with a syringe and a second end adapted to mate with a needle. The sterile end to be mated to the syringe is enclosed by a cap, which is non-permanently fixed, as for example by stick-welding or a frangible adhesive tape, to the base such that it becomes part of the package but nonetheless can be easily twisted off. Likewise, the end adapted to mate with a needle, if no needle has already been mated thereto, is non-permanently enclosed by a cap or sheath to the base, as for example also by stick-welding or a frangible adhesive tape, so as to be easily twisted off. If a needle has already been mated or molded to the second end, to maintain the needle sterile before use, the needle and the end to which it is mated or molded are enclosed by a sheath, which likewise may be non-permanently fixed to the base. Again, while providing sterile integrity to the safety needle package, the sheath can nonetheless be easily twisted off when the device is to be used. The package is further configured such that the housing coupled thereto is pivotable to a position along the longitudinal axis of the needle to envelop the same, once the sheath has been removed. The housing had previously been configured to extend away from the sheath so that no additional actions are needed to pivot it out of the way to remove the sheath and use the needle. Since both ends of the safety needle package are sealingly enclosed, both the end which mates with the needle (and of course the needle if it has already been connected thereto) and the end which mates with the syringe remain sterile. Further, since no additional containment pouches or wrappings are required, the package of the present invention takes up less space and therefore more than a few of them may be carried by a user at any one time. And without having to tear a containment pouch before usage, the safety needle device of the present invention is convenient to use.

Another aspect of the present invention safety package relates to the design at the end of the base adapted to mate with a needle which provides for automatic loosening of the sheath enclosing the needle. Thus, instead of needing to apply a large force to remove the sheath from the needle, only a gentle force is required. Such design eliminates the potential burring of the tip of the needle which results from the jerking movement of the sheath as it is removed from the needle when a large force is used.

Yet a third aspect of the invention relates to the permanent retention of the housing at a position in alignment along the longitudinal axis of the needle (or the base of the cartridge) such that a used or contaminated needle is not exposed. To accomplish this end, a first embodiment uses locking means in the form of at least one hook, integral of the housing, which permanently locks onto the needle once the housing is pivoted to its alignment position, to thereby prevent relative movement between the needle and the housing. A second embodiment of this aspect of the present invention involves the cooperative mating of an opening at the lower part of the housing to a corresponding anchor at the base of the cartridge such that once the housing is pivoted to its alignment position and the anchor lockably projected into the opening, the housing is fixedly maintained at the alignment position. No hook is used in this embodiment. Such embodiment therefore prevents any contact between the contaminated needle and the housing to thereby enable less costly manufacture of smaller and/or thinner needles, and also prevent any atomizing of potential contaminated droplets of fluid collected at the tip of the needle, which could happen were the housing hook to contact and snap onto the needle as in the previous embodiment. A variant of the third aspect embodiment of the present invention provides at least two opposed openings at the bottom portion of the housing which cooperate with corresponding locking tabs extending from appropriate portions of the base such that once the housing is pivoted to the alignment position and the respective tabs snapped into the corresponding openings, the housing is locked into place at the alignment position.

It is therefore an objective of the present invention to provide a safety package that is both convenient to use and transport.

It is yet another objective of the present invention to provide a safety package that remains sterile, yet at the same time takes up less space than prior art packages.

It is yet a further objective of the present invention to provide a different locking mechanism which fixedly retains the housing at a desirable position to envelop the needle.

BRIEF DESCRIPTION OF THE FIGURES

The above-mentioned objectives and advantages of the present invention will become apparent and the invention itself will best be understood by reference to the following description of an embodiment of the present invention taken in conjunction with the accompanying drawings, wherein:

FIG. 2A is a side view of the base and housing of the present invention, sans the needle and the enclosure cap and sheath;

FIG. 2B is a top view of the FIG. 2A needle protection device;

FIG. 2C is a cross sectional view of FIG. 2B along view A—A;

FIG. 3A is a side view of the sheath for enclosing the needle and the end of the base member to which the needle is mated;

FIG. 3B is a cutaway cross sectional view of the FIG. 3A sheath;

FIG. 3C is an end view of the FIG. 3A sheath;

FIG. 4A is an end view of the cap for enclosing the end of the base member to which a syringe is mated;

FIG. 4B is a cutaway cross sectional view, along line B—B of the FIG. 4A end view, of the present invention cap;

FIG. 4C is an end view looking into the opening of the FIG. 4B cap;

DETAILED DESCRIPTION OF THE PRESENT INVENTION

Figure 1:
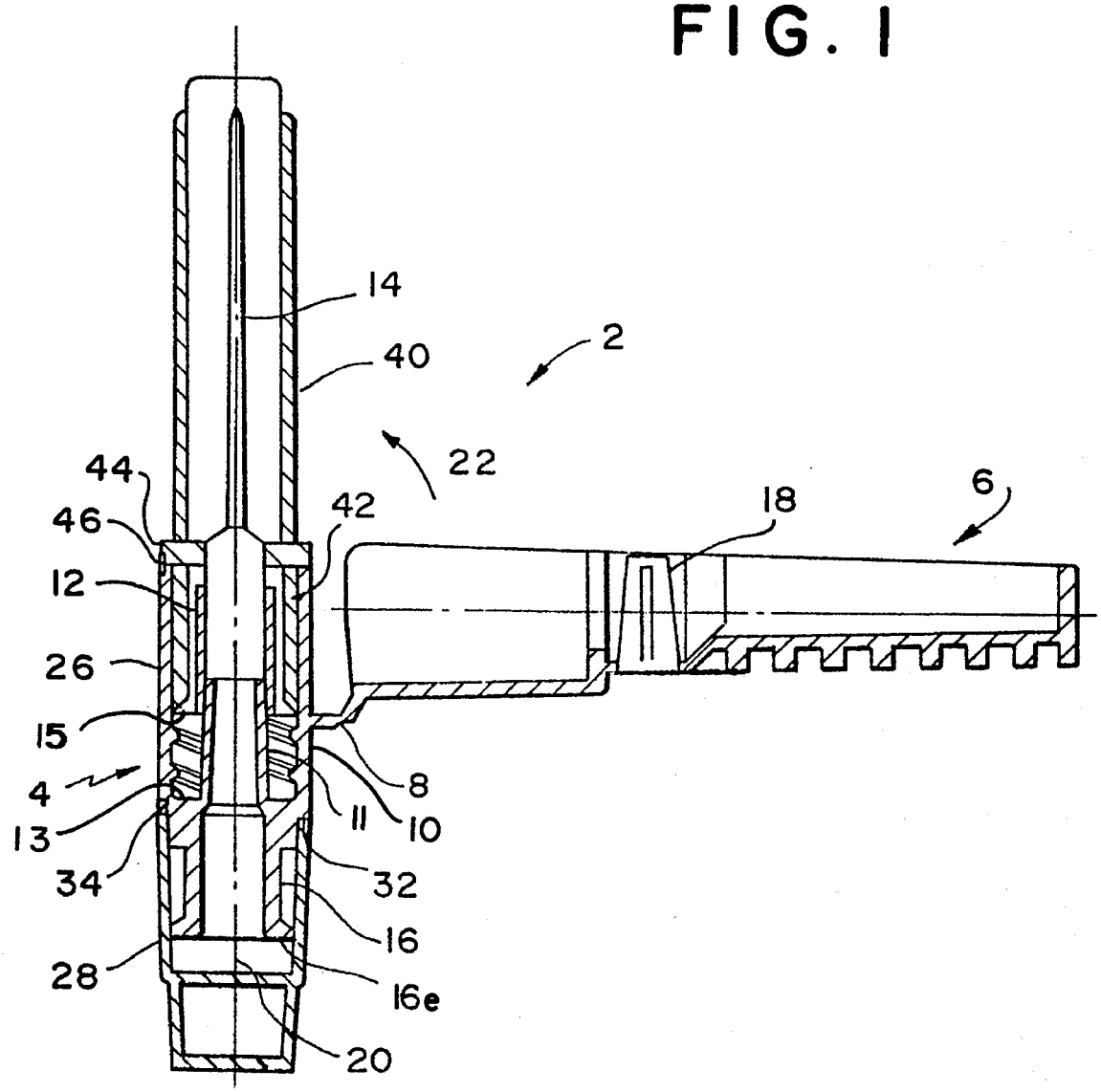
FIG. 1 is a cutaway side view of the device of the present invention.

With reference to FIG. 1, the safety needle protection package (cartridge) 2 of the present invention is shown. As illustrated, package 2 has a base 4 to which a housing 6 is hingedly attached via a living hinge 8. Base 4 has an end portion 10 for receiving hub 12 of a needle 14 of a needle assembly. It should be noted that needle 14 may actually be integrated to end portion 10 or added to end portion 10 later. As shown in FIG. 1, end portion 10 comprises a protrusion 11 extending from a support 13 of base 4. Extending from support 13 and surrounding protrusion 11 is a portion 26, the lower half of which is internally threaded for receiving extension arm 15 of hub 12.

Base 4 further has another end portion 16 which is adapted to mate with a syringe (not shown). Integrated to housing 6 is a secure means 18 which, for example, may be configured into the shape of a hook, as that shown in FIG. 2C. Housing 6 can be pivoted from the direction as shown in FIGS. 1 and 2A to a direction substantially aligned along the longitudinal axis of needle 14 or base 4, designated 20, per the direction indicated by directional arrow 22. Slot 19 (see FIG. 2B) provides the opening through which needle 14 passes when housing 6 is pivoted per direction 22. Thus, housing 6 is pivotable, as shown in FIG. 2A, per bi-directional arrows 24.

The construction of base 4 and housing 6, as well as their relationship to needle 14, is discussed in detail in Hollister U.S. Pat. No. 4,982,842, assigned to the same assignee as the instant invention and whose disclosure is incorporated herein by reference.

To provide convenience for transport and use, and at the same time maintain sterility, base 4 has fitted thereto at its end portion 16 a cap 28 whose different views are more clearly shown in FIGS. 4A–4C. As shown in FIG. 4C, opening 30 of cap 28 fittingly mates with end portion 16, particularly at its extension 16e so that cap 28 completely encloses end portion 16. To maintain the integrity of this enclosure, cap 28 is non-permanently fixed to base 4, as for example by a stick-weld made at a point 34 between lip 32 of base 4 and cap 28, or a frangible adhesive tape wrapped about the junction of lip 32 and cap 28. See FIG. 1. Cap 28 may be configured with ridges 36 along its side walls to enable a user to easily twist and remove the same from member 4. Instead of ridges, longitudinal extensions such as 38 may also be used.

To maintain needle 14 in a sterile condition and, at the same time prevent needle sticks, a sheath 40, more clearly shown in FIGS. 3A–3C, encloses both needle 14 and end portion 10 of base 4. As shown in FIG. 1, member 42 of sheath 40 which extends from lip 44 fittingly mates with portion 26 of base 4 such that both needle 14 and a portion of protrusion 11 are enveloped by sheath 40. In the instance where needle 14 is to be mated to end portion 10 later, only protrusion 11 is covered by sheath 40 as the latter fittingly mates with portion 26. As with cap 28 and end portion 16, sheath 40 is non-permanently fixed to portion 26 of member 4 by, for example, a stick-weld at 46 or a frangible adhesive tape wrapped thereabout. By providing longitudinal extensions 48 along the length of sheath 40, a user can twist sheath 40 off base 4 for removal. See FIG. 3B. Needle 14 could then be mated to end portion 10 at that time if it had not been mated thereto previously. It should be noted that cap 28 and sheath 40 could be produced by a host of manufacturers, as for example the Sherwood Medical Company of Deland, Fla.

Once base 4 has fitted thereto at its respective end portions 16 and 10 corresponding cap 28 and sheath 40, safety needle package 2 can be sterilized by conventional methods, as for example by conventional radiation or chemical treatments. Once having been sterilized, safety needle device 2 can be carried or transported without any need for a protective containment pouch or wrapper, as the sterility of needle 14 and end 16 are ensured by sheath 40 and cap 28, respectively.

Assuming needle 14 had previously been mated to end portion 10, to use safety device 2, a user only needs to twist and remove cap 28 from base 4, couple a syringe to end 16, and remove sheath 40. If needle 14 had not previously been mated to end portion 10, it can be added to base 4 at end portion 10 after sheath 40 has been removed from base 4. After usage, housing 6 is pivoted along direction 22 to a position substantially in alignment along longitudinal axis 20 so that needle 14 is secured by hook 18 and relative movement is prevented between needle 14 and housing 6.

Figure 5:
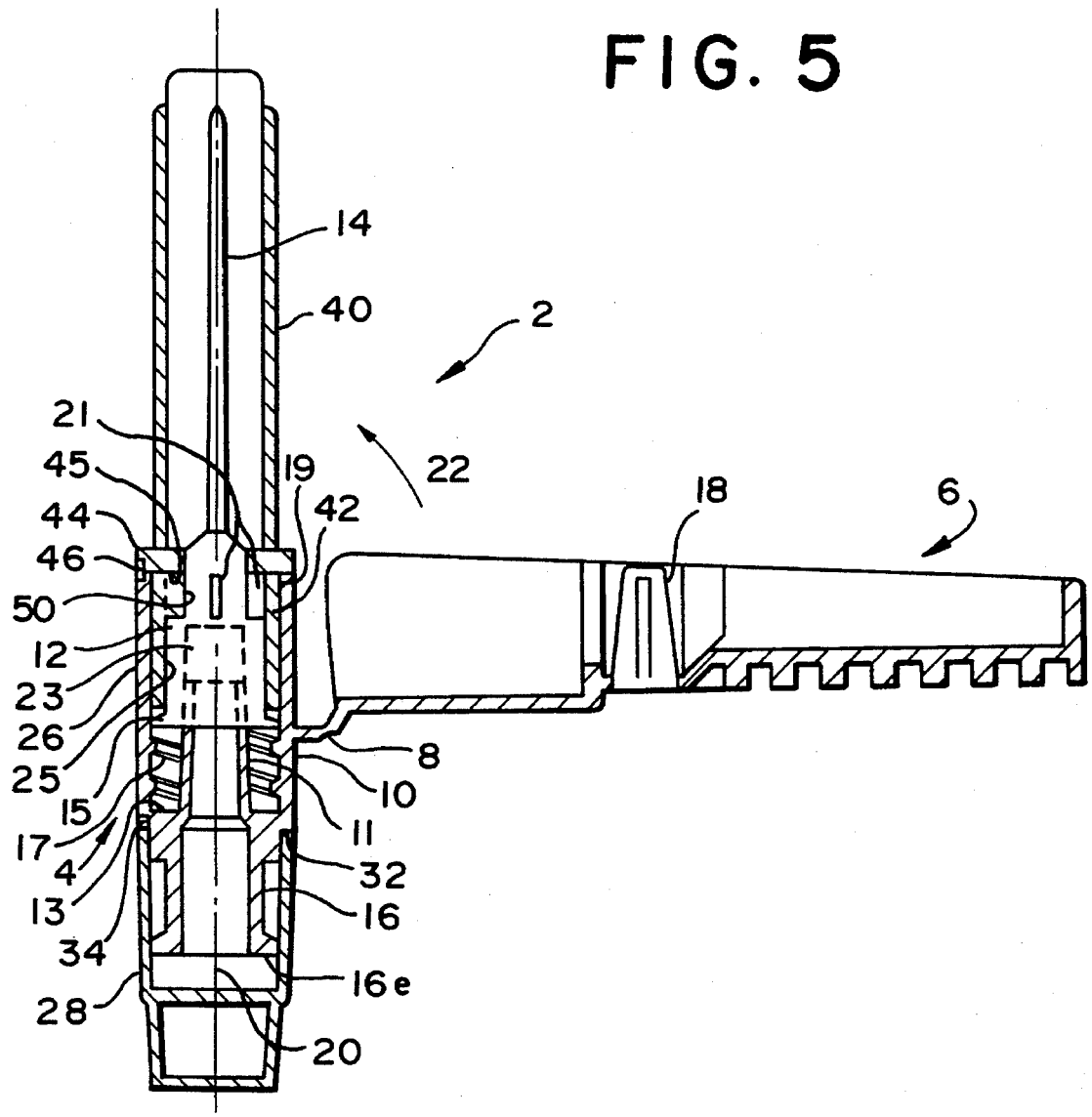
FIG. 5 is a semi-cutaway side view of the present invention illustrating in particular a design that advantageously provides automatic loosening of the needle sheath of the hub of the needle so that the former is easily removed from the latter.

A second aspect of the safety package of the present invention is illustrated in FIG. 5 where needle 14 is presumed to have been mated to end portion 10. The FIG. 5 embodiment is necessitated by the fact that if sheath 40 were to be separated from needle 14 by pulling, the force required tends to cause a jerking motion, inasmuch as needle hub 12 is tightly fitted to member 42 of sheath 40. Such jerking motion oftentimes causes the tip of needle 14 to touch the inside of sheath 40 which results in a burr to the tip of needle 14.

To prevent burring of the tip of needle 14, as shown by the FIG. 5 embodiment, needle hub 12, tightly fitted to member 42 of stealth 40, as it is inserted to end portion 10 and mate with protrusion 11 during assembly, threadedly mates with an internal thread 17 surrounding protrusion 11 via extender arm 15. In other words, external arm 15 of hub 12 is threaded approximately 1 turn into internal thread 17 to secure needle 14 to base 4. At this point, needle hub 12 remains tightly fitted to member 42 of sheath 40 while needle sheath 40 is non-permanently fixed to base 4 by, for example a stick-weld at point 46.

The design of sheath 40 is such that lip 44 has a bottom face 45 that coacts with tip 19 of base 4 at the area proximate to point 46. Thus, sheath 40 is prevented by lip 44 from being inserted any further into base 4. Extending internally below lip 46 of sheath 40 is a plurality of extenders 50. See FIG. 3B. These extenders 50 come into contact with a plurality of partitions 21 extending from the top portion of needle hub 12. Thus, a torque force applied to sheath 40 causes hub 12 to rotate in tandem.

For the FIG. 5 embodiment, when shipped, sheath 40, with needle 14 tightly fitted thereto and securely mated to base 4 via thread 17, is non-permanently fixed to base 4 at point 46. To ensure that no force is needed to jerkingly separate sheath 40 from hub 12, a user only needs to twist sheath 40 (clockwise assuming conventional threads) so that extender arm 15, and therefore hub 12, is threaded toward support 13 via internal thread 17. As hub 12 is threaded toward support 13, protrusion 11 is extended further into cavity 23 of hub 12, as hub 12 is pulled closer toward support 13. At the same time, sheath 40 remains in the same relative position, insofar as lip 44 remains biased against tip 19 of base 4. Thus, as sheath 40 is rotated, due to cooperation between extenders 50 of sheath 40 and partitions 21 of hub 12 and the biasing between lip 44 and tip 19, hub 12 is automatically loosened and separated from sheath 40. Once hub 12 is firmly or fully seated, sheath 40 can be easily removed from hub 12 by a gentle straight pull, which does not cause the interior of sheath 40 to come into contact with the tip of needle 14.

Albeit the FIG. 5 embodiment shows that the internal surface of member 42 is contiguous with the external circumferential surface of hub 12, as for example at junction 25, it should be appreciated that hub 12 and member 42 can be designed so that hub 12 is tightly fitted to member 42 at only one common point, as for example by a corresponding ring and groove configuration. The FIG. 5 embodiment shows that sheath 40 is non-permanently fixed to base 4 with hub 12 not fully seated toward support 13. Of course, sheath 40 can be non-permanently fixed to base 4 after hub 12 is fully threaded. At which case a counterclockwise rotation would break the seal at 46.

Figure 6:
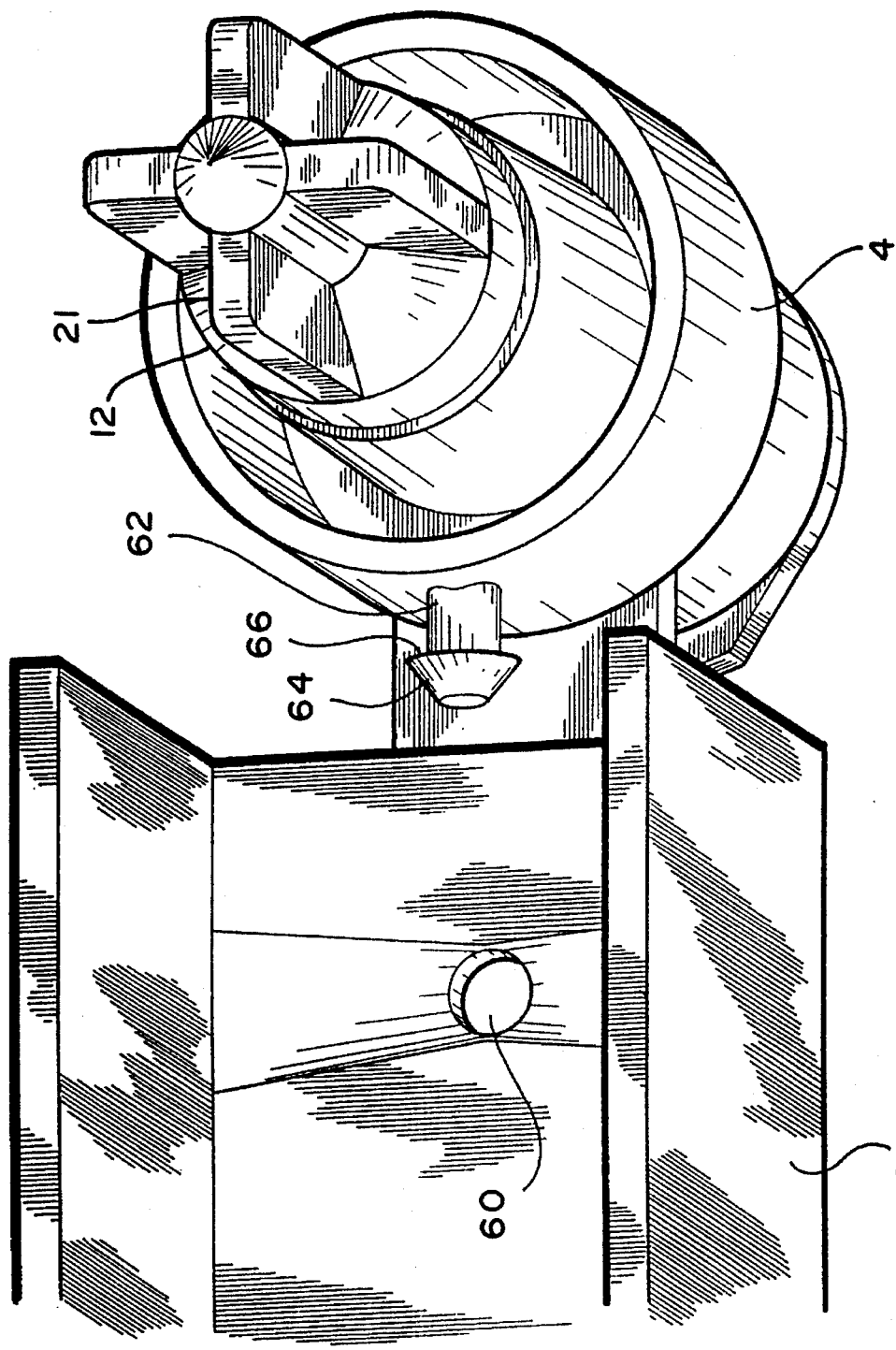
FIG. 6 is an enlarged partial perspective view of the base and housing of the present invention package in which the locking mechanism for maintaining the housing at a position in alignment with the needle for enveloping the same comprises an opening at the lower portion of the housing cooperating with an anchor extending from an appropriate portion of the base.

Yet a third aspect of the safety package of the present invention is illustrated with respect to FIG. 6. In place of hook 18 as shown in FIGS. 2A–2C which snaps onto needle 14 to prevent relative movement between it and housing 6 as discussed above, the FIG. 6 variant has an anchor 62 protruding from base 4 which works cooperatively with an opening 60 at the lower portion of housing 6. When housing 6 is pivoted to the position substantially in alignment with needle 14, anchor 62 would be projected through opening 60 to thereby fixedly retain housing 6 at the alignment position. In particular, as shown, anchor 62 has a graduated tip portion 64 whose base 66 is larger than the diameter of opening 60. And inasmuch as base portion 64 is elastic and can be forced through opening 60, once housing 6 is pivoted to its alignment position, it is prevented from further substantial movement relative to base 4, as base 66 prevents any reverse pivotal movement by housing 6. Thus, once pivoted to the alignment position and locked to anchor 62, needle 14 (not shown in FIG. 6 for the sake of clarity) is substantially enclosed by housing 6. Of course, housing 6 of the FIG. 6 embodiment does not have any hooks such as 18 shown in FIGS. 1, 2 and 5 integrated thereto. Thus, by not making any contact with needle 14 as housing 6 is pivoted to the alignment position, spraying of potentially contaminated droplets of fluid which may have adhered to the tip of needle 14 is prevented. Furthermore, insofar as no forced contact is made to needle 14 as housing 6 is pivoted to its alignment position, a thinner needle, which if used in the FIG. 1 embodiment would have buckled, could be manufactured instead, to thereby lower the manufacturing cost.

Figure 7:
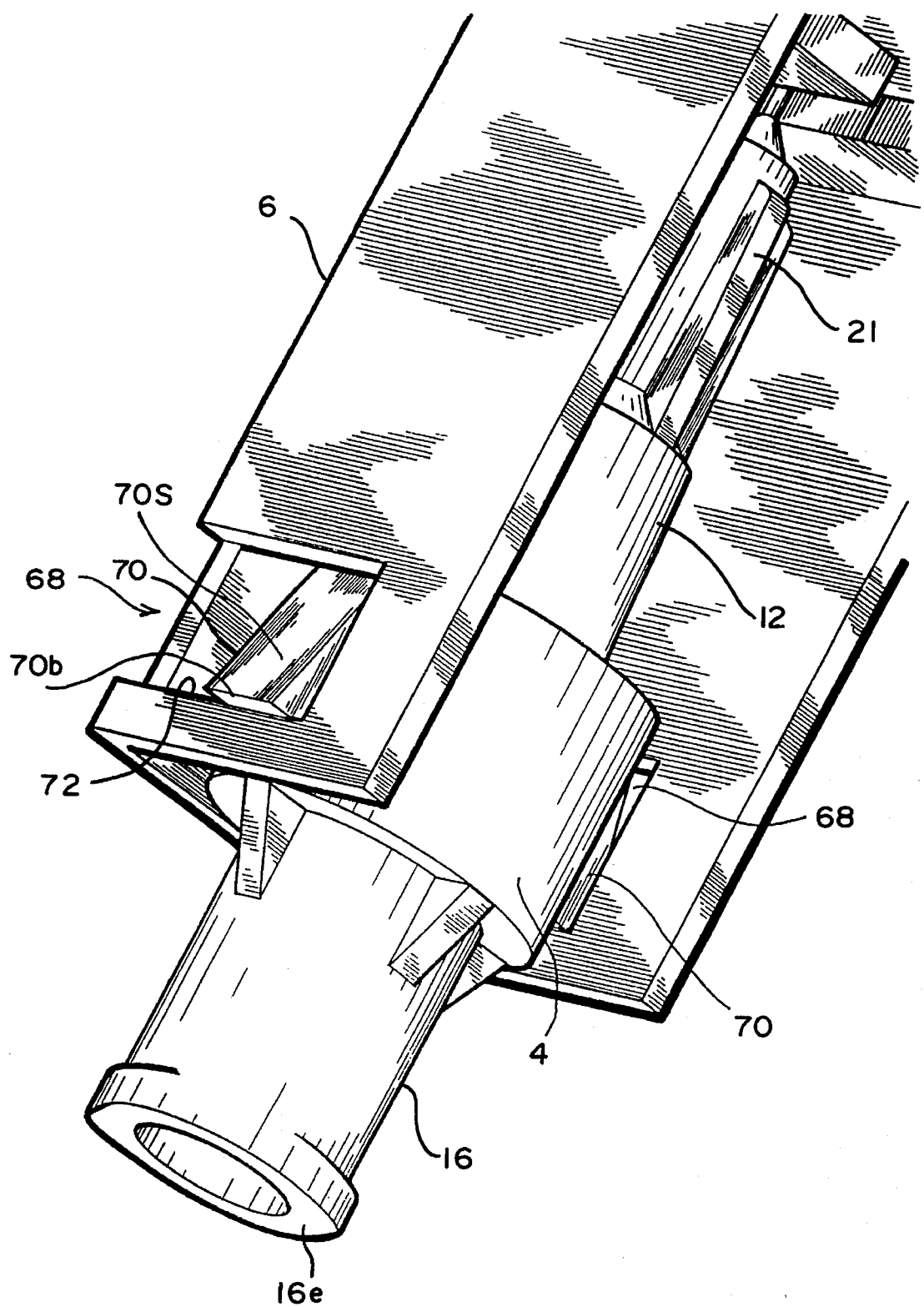
FIG. 7 is an enlarged partial perspective view of a variant of the locking mechanism of the instant invention in which the needle housing is maintained at the alignment position by two cooperative openings/tabs.

A variant of the FIG. 6 embodiment is illustrated in FIG. 7 in which housing 6 is shown to have been pivoted to its alignment position to enclose needle 14. As shown, housing 6 has two opposed openings 68, one fully shown and the other partially shown. With reference to the fully shown opening 68, it can be seen that the opening is made at the lower portion of housing 6 and extends from the back of housing 6 to proximately the medial portion of its side pane. A pair of corresponding locking tabs 70 are formed at corresponding portions of base 4. Each tab 70 has a slanting surface 70s which gradually increases, in terms of its extension along base 4, from top to bottom. Thus, as shown, tab 70 has a base portion 70b that extends beyond the face of the side pane of housing 6 such that housing 6 is fixedly retained at its alignment position, once it is pivoted thereto, by the coaction between edge 72 of housing 6 and base 70b of tab 70. Thus, similar to the discussion with respect to the FIG. 6 embodiment, there is no contact made between housing 6 and needle 14 as the former is pivoted toward the latter. Accordingly, for the FIG. 7 embodiment, needle 14 likewise may be manufactured to have a thinner gauge and any splattering of contaminated fluid droplets at the tip of needle 14 is prevented.

Inasmuch as safety needle package 2 does not require any additional packaging and therefore is not bulky, the user can conveniently carry a number of them with him for use. And since there is no need to tear any pouch or other containment wrapping, precious time can be saved in emergency situations in which time is of the essence, as all a user needs to do is remove cap 20 and sheath 40, and connect a syringe to end portion 16. In addition, without having to individually package each needle protection device, potential savings could be achieved during manufacturing.

It should be appreciated that the present invention is subject to many variations, modifications and changes in detail. For example, instead of stick-welding cap 28 and sheath 40 to base 4, other adhesive methods which would maintain the sterile condition and integrity of the package may also be used. For example, instead of two frangible tapes to respectively seal sheath 40 and cap 28 to base 4, a single frangible tape sealing the area about junctions 46 and 32 could be used. Thus, it is the intention of the inventor that all matter described throughout this specification and shown in the accompanying drawings be interpreted as illustrative only and not in a limiting sense. Accordingly, it is intended that this invention be limited only by the spirit and scope of the hereto appended claims.

I claim:

1. A safety package comprising:

a base having a first end matable with a syringe and a second end matable with a needle assembly;

cap means for enclosing said first end;

sheath means for enclosing said second end, said sheath means being fitted to said second end;

housing means hingedly attached to said base and pivotable to a position to be in substantial alignment along the longitudinal axis of said base;

wherein said needle assembly comprises a needle attached to a hub;

wherein after said sheath means has been removed from said second end and said needle assembly mated thereto, said housing means pivotable for substantially enveloping said needle mated via said hub to said second end; and wherein said sheath means encloses at least a portion of said needle assembly including a needle, said second end of said base comprises an internal thread for receiving a hub of said needle assembly, said sheath means having a first portion cooperatively biasing against a second portion of said base so that when said sheath means is rotated to fully thread said hub into said base, said sheath means is automatically loosened from said hub for easy removal from said needle.

2. A safety package comprising:

a base having a first end matable with a syringe and a second end matable with a needle assembly;

cap means for enclosing said first end;

sheath means for enclosing said second end, said sheath means being fitted to said second end;

housing means hingedly attached to said base and pivotable to a position to be in substantial alignment along the longitudinal axis of said base;

wherein said needle assembly comprises a needle attached to a hub;

wherein after said sheath means has been removed from said second end and said needle assembly mated thereto, said housing means pivotable for substantially enveloping said needle mated via said hub to said second end; and wherein said housing means comprises at least one opening matable with an anchor means integrated to said base such that once said housing means is pivoted to said alignment position and said anchor means lockably projected through said opening, said housing means is substantially fixedly retained at said alignment position.

3. A safety package comprising:

a base having a first end matable with a syringe and a second end matable with a needle assembly;

cap means for enclosing said first end;

sheath means for enclosing said second end, said sheath means being fitted to said second end;

housing means hingedly attached to said base and pivotable to a position to be in substantial alignment along the longitudinal axis of said base;

wherein said needle assembly comprises a needle attached to a hub;

wherein after said sheath means has been removed from said second end and said needle assembly mated thereto, said housing means pivotable for substantially enveloping said needle mated via said hub to said second end; and wherein said housing means comprises at least two opposed openings at its lower portion each of which, when said housing means is pivoted to said alignment position, cooperatively mates with a corresponding extension integrated to said base such that said housing means is substantially fixedly retained at said alignment position.

4. A safety package comprising:

a base having a first end adapted to mate with a syringe and a second end adapted to mate with a needle mounted to a hub;

cap means for enclosing said first end;

sheath means fitted about said hub for enclosing said needle, said hub of said needle mated to said second end of said base;

housing means hingedly attached to said base;

wherein after said sheath means is removed from said needle, said housing means being pivotable to a position in substantial alignment along the longitudinal axis of said needle for enveloping said needle; and wherein said second end of said base is internally threaded for mating with said hub, said sheath means having a first portion biased against a second portion of said base so that said first and second portions would coact against each other to loosen said sheath means from said hub for easy removal when a torque force is applied to substantially seat said hub to said second end.

5. The safety package of claim 4, wherein said housing means comprises at least one opening matable with an anchor means integrated to said base such that once said housing means is pivoted to said alignment position and said anchor means lockably projected through said opening, said housing means is substantially fixedly retained at said alignment position to prevent said needle from being exposed.

6. The safety package of claim 4, wherein said housing means comprises at least two opposed openings at its lower portion each of which, when said housing means is pivoted to said alignment position, cooperatively mates with a corresponding extension integrated to said base such that said housing means is fixedly retained at said alignment position to prevent said needle from being exposed.

7. A safety package comprising:

a base having a first end adapted to mate with a syringe and a second end matable with a needle assembly;

cap means for enclosing said first end;

sheath means for enclosing said second end;

housing means hingedly attached to said base and pivotable to a position in substantial alignment along the longitudinal axis of said base;

wherein after said sheath means is removed from said second end, said housing means pivotable for substantially enveloping a needle mated to said second end, said housing means comprising at least one opening matable with an anchor means integrated to said base such that once said housing means is pivoted to said alignment position and said anchor means lockably projected through said opening, said housing means is substantially fixedly retained at said alignment position.

8. The safety package of claim 7, wherein said sheath means is tightly fitted to a hub of said needle; and wherein said second end of said base comprises an internal thread for receiving said hub, said sheath means having a first portion biased against a second portion of said base so that when said hub is substantially threaded into said base, said first and second portions would cooperatively act against each other to loosen said sheath means from said hub for easy removal from said needle.

9. A safety package comprising:

a base having a first end adapted to mate with a syringe and a second end matable with a needle assembly;

cap means for enclosing said first end;

sheath means for enclosing said second end;

housing means hingedly attached to said base and pivotable to a position in substantial alignment along the longitudinal axis of said base;

wherein after said sheath means is removed from said second end, said housing means pivotable for substantially enveloping a needle mated to said second end, said housing means comprising at least two opposed openings at its lower portion each of which, when said housing means is pivoted to said alignment position, cooperatively mates with a corresponding extension integrated to said base such that said housing means is fixedly retained at said alignment position.

10. The safety package of claim 9, wherein said sheath means is fitted to a hub of said needle; and wherein said second end of said base comprises an internal thread for receiving said hub, said sheath means having a first portion biased against a second portion of said base so that when said hub is substantially threaded into said base, said first and second portions would cooperatively act against each other to loosen said sheath means from said hub for easy removal from said needle.

* * * * *